US007465829B2

(12) United States Patent
Schneider et al.

(10) Patent No.: US 7,465,829 B2
(45) Date of Patent: *Dec. 16, 2008

(54) HALO ACTIVE AROMATIC SULFONAMIDE ORGANIC COMPOUNDS AND USES THEREFOR

(75) Inventors: Charles A Schneider, Villa Hills, KY (US); David J. Schneider, Union, KY (US)

(73) Assignee: Schneider Advanced Technologies, Inc., Covington, KY (US)

(*) Notice: Subject to any disclaimer, the term of this patent is extended or adjusted under 35 U.S.C. 154(b) by 821 days.

This patent is subject to a terminal disclaimer.

(21) Appl. No.: 10/369,175

(22) Filed: Feb. 18, 2003

(65) Prior Publication Data
US 2003/0162755 A1    Aug. 28, 2003

Related U.S. Application Data

(60) Provisional application No. 60/357,265, filed on Feb. 19, 2002.

(51) Int. Cl.
C07C 303/00    (2006.01)
C07C 255/00    (2006.01)

(52) U.S. Cl. .............. 564/84; 564/90; 564/99; 558/413

(58) Field of Classification Search ........... 558/913; 564/99, 84, 90
See application file for complete search history.

(56) References Cited

U.S. PATENT DOCUMENTS 2,809,937 A * 10/1957 Gray ............... 510/382
3,888,897 A *  6/1975 Martin ............. 558/413
6,296,841 B1 * 10/2001 Schneider ......... 424/76.1

FOREIGN PATENT DOCUMENTS

JP    10081610    * 9/1998 ............ 558/413

OTHER PUBLICATIONS

Chrzasczewska et al PL 52046( CA 69:18848 Best Available).*
FDA , Dry Milk Ordinance Supplement 1 Appendix B pp. 87-88 (1995).*
Mullen, The Biocides Business: Regulation, Safety and Applications, pp. 251-266, (2002).*
Dawson et al, Inter. Ass. Fish & Wildlife, Approval of Drugs for Public fish Production, Second Mids-Year Report of Progress, pp. 1-11.*

* cited by examiner

Primary Examiner—Janet L. Andres
Assistant Examiner—Raymond Covington
(74) Attorney, Agent, or Firm—Richard M. Klein; Fay Sharpe LLP (57) ABSTRACT

Halo active aromatic sulfonamide organic compounds have been known for over one hundred years. The ability of these compounds to releaser active halogen ions has been utilized in a range of biocidal and fungicidal applications. The most widely used sulfonamide organic compound for these applications has been Chloramine T. This invention deals with nearly discovered halo active aromatic sulfonamide organic compounds and uses of these compounds as biocides, odor control agents, bovine teat cleaners, drugs for cultured fish, soap biocides, stain removal agents, and paint fungicides.

28 Claims, 7 Drawing Sheets

HALO ACTIVE AROMATIC SULFONAMIDE ORGANIC COMPOUNDS AND USES THEREFOR

RELATED APPLICATIONS

This application claims priority of Provisional application Ser. No. 60/357,265 filed Feb. 19, 2002.

BACKGROUND OF THE INVENTION

Halo active aromatic sulfonamide organic compounds have been known for well over one hundred years. These compounds have been put to a wide range of uses. These include uses as fungicides, biocides, odor control agents, drugs, reaction intermediates, etc. A widely used sulfonamide organic compound is Chloramine T. This invention relates to a new class of halo active aromatic sulfonamide organic compounds which have better properties and less side effects than the compounds of the prior art. In a broad sense it could be said that many of halo active sulfonamide compounds of this invention are more active and are less toxic than the sulfonamide compounds of the prior art.

The new compounds of this invention show improved properties as biocides, fungicides, odor control agents, drugs for cultured fish, paint additives, soap additives, stain removal agents and teat cleansers.

When the new halo active aromatic sulfonamide compounds of this invention are used as a biocide, fungicide, odor control agent, or as a teat cleanser, solutions of the sulfonamide compound are brought into contact with the surface being treated. This contact is usually effected by spraying the surface with an aqueous solution of the desired sulfonamide compound.

PRIOR ART

U.S. Pat. No. 6,296,841 discloses the use of Chloramine T as an odor control agent wherein the Chloramine T is used with a wetting agent. The disclosure relates primarily to domestic odor control.

A related U.S. patent application Ser. No. 09/957,230 discloses the use of Chloramine T as an odor control agent wherein the Chloramine T is used with and without a wetting agent. The disclosure relates to domestic and industrial odor control.

U.S. Pat. No. 6,386,145 relates to the use of low dosages, of Chloramine T, on a continuous basis, to cure bacterial infections in cultured fish. Prior art methods for curing bacterial infections in cultured fish are also disclosed.

BRIEF DESCRIPTION OF THE INVENTION

This invention has several aspects which include new compositions of matter, a new process for killing bacteria, a new process for killing fungi, new soap formulations, a new process for killing odors, new paint formulations, new teat cleansers, stain removal agents and a new process for treating diseased fish.

The new compositions of matter are halo active aromatic sulfonamide organic compounds which will be defined in greater detail herein below. These new compositions of matter posses excellent biocidal and fungicidal properties. These properties lend these new compositions of matter to a wide range of uses.

Further the new compositions of matter of this invention have the ability to react with odorous sulfur heterocyclic and nitrogen containing compounds and mixtures thereof, in such a manner as to convert these compounds to a non odorous format. That is the new compounds are useful as odor control agents.

In accordance with one embodiment of this invention the new compositions of matter are used as a biocide to kill bacteria.

As per still another embodiment of this invention the new compositions of matter are useful as fungicides. These fungicidal properties make the new compositions of matter of this invention useful as paint additives.

This invention also includes soap formulations which kill bacteria as a result of the above described biocidal properties.

Because of their low toxicity the new compositions of matter are useful as teat cleansers in the dairy art.

The composition of this invention are also useful as stain removal agents.

Likewise because of their low toxicity and excellent biocidal properties many of the new compositions of matter, of this invention, are excellent drugs for diseased cultured fish.

Further this invention relates to the removal of stains from textiles.

DESCRIPTION OF THE PREFERRED EMBODIMENTS

Composition of Matter

Halo active aromatic sulfonamide organic compounds have been known and used for over one hundred years. Chloramine T is an example of an old sulfonamide organic compound which has been used in many applications. The usefulness of Chloramine T is predicated on its ability to release an active Cl+ ion which makes it useful in the biocidal of fungicidal arts.

The halogen ion released by halo active aromatic sulfonamide organic compounds of this invention are relativity covalent. This relative covalency prevents the Cl+ ion from having detrimental bleaching properties.

The new halo active aromatic sulfonamide compounds of this invention have excellent biocidal, fungicidal and odor control properties. In addition many of these compounds have excellent toxicity properties which makes there usage as biocides and fungicides, acceptable in human, animal and aquatic environments.

The above described usages and properties will be described in greater detail herein below. The new halo active aromatic sulfonamide compounds in accordance with this invention are in accordance with the following Formula I.

FORMULA I

Wherein;
X is a halogen,
$R_1 R_2$ and $R_5$ are COOH, $NO_2$, $HSO_3$, COOM a halogen, hydrogen an Aliphatic or branched entity from $C_2$ to $C_{12}$, an esterfied alkylated amide or a fully alkylated amide,
$R_3$ and $R_4$ are the same as $R_1$, $R_2$ and $R_5$ except that an aliphatic moiety may not contain an alpha hydrogen and,
M is an alkali or alkaline earth metal.

FORMULA II

Wherein,
$R_1$ is COOH, $NO_2$, $HSO_3$, COOM, a halogen, an aliphitic or branched entity from $C_2$ to $C_{12}$, an esterfied alkylated amide or a fully alkylated amide,
X is chlorine, fluorine, bromine or iodine and,
M is sodium or potassium.
A most preferred halo active aromatic sulfonamide compound in accordance with this invention is in accordance with Formula III.

FORMULA III

Wherein
$R_1$ is COOH or COOM
X is chlorine and M is sodium.
The compounds as are set forth by Formulas I-III above are very stable and in particular they do not decompose in aqueous solutions. This property is advantageous in that products which are compounded of Formulas I-III have long shelf lives.

The compounds of Formula I-III are very soluble in water, this property allows for easy compounding of products and allows high percentages of the compound to be compounded into solution products.

Further the compounds of Formulas I-III have minimal bleach odor. This property is advantageous as in products for household use, a strong bleach odor is undesirable.

The activity of the sulfonamide group of the compounds of Formula I can be regulated by the selection of the groups which comprise R3 and R4. That is group R3 and R4 can effect steric hindrance on the sulfonamide group.

In the following discussion the above set forth Formula I, Formula II and Formula III will be referenced.

As is discussed above the new compounds as discussed above are useful in a wide variety of arts. These arts include odor control, bacteria control, fungus control, soap formulations, paint formulations, the dairy cleansing art, stain removal and the aquatic disease control arts.

As to these uses for the new halo active aromatic sulfonamide compounds of this invention the following should be noted.

Odor Control

Halo active aromatic sulfonamide organic compounds for use in odor control are known in the prior art. In this regard Chloramine T has been used in odor control compositions see the above set forth discussion, relative to U.S. Pat. No. 6,296, 841 and the disclosure of application Ser. No. 09/957,230.

In accordance with the above discussion this invention is concerned with use of the new compounds of this invention for controlling odors in household, institutional and industrial applications. Perfumed odor control compositions have been used for thousands of years however these solutions did not destroy the odorous materials but instead they only mask the odors caused by these materials. In contrast to this masking of the troublesome odorous material in the prior art, the new sulfonamide compounds and process of this invention react with the odorous molecules. In the prior art odor control compositions are perfumes wherein the odors are masked with synthetic or natural essence. In the subject invention, instead of masking the odor with a perfume, the odor causing molecules are degraded by reaction with a Cl+ moiety and with the chemical moiety which remains after the Cl+ moiety is removed from the new sulfonamide compounds of this invention. The use of Cl+ is common in odor control, the most common Cl+ producing composition is household bleach. The preferred source of a Cl+ moiety for use in accordance with this invention are the new compounds as are represented by Formulas I-III, as are set forth above.

Bleach is commonly used as a source of Cl+ cations which are useful as deodorizers. Because of the problems associated with the use of bleach, i.e. the discoloration of the substrate, heavy, non discrete and detrimental oxidizing power, it is generally not suitable for use as a deodorizer. In addition the Cl+ cation which is produced by bleach is much more ionic and non discrete in its reactions when compared to the Cl+ cation produced by the compounds of Formulas I-III. When compared to the Cl+ cation produced by bleach the Cl+ cation produced by the compounds of Formulas I-III is much more covalent and less ionic and therefore is very selective in its reactions as a deodorizer, that is it attacks the odor source and not the substrate. As a result of this covalence the side effects produced by the Cl+ cation produced by the compounds of Formulas I-III are not as severe as those produced by bleach. Therefore the Cl+ cation produced by the compounds of Formulas I-III can be used to deodorize as they do not have side effects such as strong bleach smell, the undesirable bleaching of the odor containing substrate etc. Further the compounds of Formulas I-III are more stable than bleach and have a higher Cl+ activity as compared to the Cl+ cation produced by bleach.

When compared to bleach the compounds of Formulas I-III are a superior deodorizing agents because they are more selective and more covalent. Further the backbone, remaining after the Cl+ cation is released from the compounds of Formulas I-III, reacts with the odor containing molecule thereby permanently removing it as a potential source of odor. In contrast the chemical moiety which remains after the Cl+ cation is removed from bleach has no ability to react with odor causing molecules.

Most odor causing molecules are mercaptans, sulfides heterocyclic or amine based compounds. The compounds of Formulas I-III are excellent agents for eliminating odors from these classes of compounds as both the Cl+ cation produced by the compounds of Formulas I-III and the residual chemical moiety remaining after the Cl+ cation is produced, react with the odor causing molecule(s).

In order for the compounds of Formulas I-III to be effective they must come into contact with the substance which is responsible for the odor. If the substance which is responsible for the odor is in an environment which makes access difficult i.e. pet stains in a carpet, a means must be provided for bringing the selected compound of Formulas I-III into contact with the odor causing substance. In many instances when aqueous solution is used as a delivery medium the solution tends to bead up on the substrate. Therefore. when the water component of the solution evaporates the substance in solution is deposited only in localized areas. In the case at hand if an aqueous solution of one of the compounds of Formulas I-III were applied to a carpet containing pet stains, the solution would bead up on the carpet, such that when the water evaporated the placement of the compound in question on the carpet would be spotty. Due to this poor placement the two reactive components of the molecule would not be in position to react with all of the odor causing substance on a molecular basis. That is the reaction of the odor control compound with the pet stain would be incomplete, and hence the odor control would be incomplete.

The use of wetting agents with various solutions in order to reduce surface tension is common in the prior art. For example wetting agents are commonly added to herbical solutions to allow the herbicide to wet out plant leaves, likewise the use of wetting agents with insecticides is common.

In accordance with one embodiment of this invention a substance is added to the solutions of this invention to reduce the surface tension of the solution. As is discussed above the selected compound of Formulas I-III functions in part by the reaction of the Cl+ moiety with the odor causing molecule. One aspect of this invention is concerned with the fact that many substances which are suitable for reducing the surface tension of the solution may adversely affect the formation of the Cl+ moiety, from the compounds of Formulas I-III or degrade said Cl+ moiety once it is formed.

Suitable substances which are useful in accordance with one embodiment of this invention for reducing the surface tension of the odor control solutions of this invention are synthetic and natural wetting agents. Wetting agents are generally classified as cationic, anionic, amphoteric and non-ionic. Because there are thousands of natural and synthetic wetting agents it is impossible to make generalizations as to which would be effective in the composition of this invention. With this caveat it can be said that generally the most preferred wetting agents for use in accordance with this embodiment of this invention are anionic wetting agents, with the next preferred class of wetting agent being a nonionic wetting agents.

Amphoteric and cationic wetting agents are least preferred for use with the wetting agent embodiment of this invention.

Regardless of the above comments satisfactory agents may be found in any class of wetting agents.

While the applicant is not sure of all ramifications of how different wetting agents degrade the Cl+ moiety functional groups such as alkenes, alcohol, ketone, especially aliphatic ketones or aldehydes containing at least one alpha hydrogen next to the carbonyl carbon are particularly detrimental to the CL+ ion. Further phenols as may be contained on the base wetting agent molecule are particularly harmful to the Cl+ moiety.

Further while it is impossible for the applicant to explore all the ramifications thereof, impurities as may be contained in various commercially available wetting agents can play a significant part in the degradation of the Cl+ moiety. Impurities which are known to facilitate the degradation of the Cl+ moiety are aromatic and conjugated phenols, compounds containing activated carbonyl, alpha aliphatic hydrogens or active primary and secondary amines.

The concentration of the wetting agent used in accordance with this invention can be from about 0.1 to 5%. A more preferred concentration for the wetting agent is from about 0.5 to about 1.5%. In order to achieve maximum efficiency in the odor control process, the surface tension of the solution must be reduced so that the compound of Formulas I-III can reach and react with the odor causing molecules.

A factor in choosing the concentration of the wetting agent is the degree to which it foams. If undesirable foaming occurs anti foamers may be added to the solution.

For stability and for optimum performance as an odor killing agent the pH of a solution of the compounds of Formula I-III should be between 6-14, with a more preferred pH range being between 8-9.5 with a most preferred range being between 8.5-9.

As is discussed above the pH range for odor control solutions for use in the invention can be from about 6-14. Below a pH of 6 the compounds of Formula I-III tends to decompose due to the acidic nature of the medium. While the solutions of this invention are effective above a pH of 10.0 solutions having a pH of above 10.0 can only be used for industrial applications, due to their caustic nature.

Sulfonamide solutions for use in this invention exhibit excellent stability at a pH range of 8-9.5. This stability is important in the domestic applications of this invention where long shelf life is very desirable.

A 5% solution of a compound of Formulas I-III naturally buffers at a range of about 8.5-9.5. In order to maintain the solution within these pH ranges, it is preferred that the solution be buffered. The buffering of the solution further compensates for any change in pH that may result from the acidity of the water which is used to make the solution, the conditions of application, the type of substrate, or industrial waste and the nature of the odor causing molecule.

Buffering agents which are suitable for use in accordance with this invention are sodium bicarbonate, potassium bicarbonate, sodium carbonate, potassium carbonate, acetate buffers (such as sodium acetate), phosphate buffers (such as tri and di sodium phosphate and mixtures thereof, pH blended phosphates, sulfate buffers (such as di and tri sodium sulfate and mixtures thereof.

Because of price, ease of use, low toxicity and their effect on the environment, the above listed sodium and potassium bicarbonate are preferred buffering agents for use in this invention. Buffered solutions are advantageous in that the active ingredients of the odor control solution of this invention can be shipped in powdered form and mixed by the consumer with no adverse effects.

The concentration of the buffering agent can be from 0% up to the limit of solubility. The preferred range for the concentration of the buffering agent is from about 5% to about 200% of the active compound in solution. A more preferred range is from about 5% to about 50% with a most preferred concentration being 25-50%.

For the industrial odor control it is preferred that the concentration of a compound of Formula I-III be about 5-10%. For residential consumer use the concentration of the active ingredient can be from about 0.25 to about 2.0%, with a more preferred range being from about 0.5 to about 1.0% percent, with the most preferred concentration being 0.75%. These lower concentrations keep the bleach like smell to a minimum but still gives the desired odor control. A strong bleach smell tends to function like a perfume in masking the undesirable odor.

The composition and process of this invention is suitable for use in controlling the odor which is emitted from a wide variety of industrial sludge such as sewerage treatment sludges, paper making sludges, waste from animal grow outs, animal processing and animal habitats etc.

Paper mills are notorious for creating foul odors. In particular the Kraft paper making process produces an odor which is often categorized as a rotten egg smell. In the past society was tolerant of these odors as society often took the position that the smell of a paper mill was the smell of money. The odor of a paper mill is primarily based on odorous mercaptans which the human nose can detect at concentrations which approach one part per billion. These paper mill odors originate from the holding ponds which are used to hold the sludge which is a byproduct of the paper making process, from the sludge which results from the treatment of the paper mill stack gases and from solid press. Odors originating with paper mills can often be detected by humans at distances which can exceed twenty miles.

While in the past society was tolerant of these odors in recent times society has become much less tolerant, therefore it is important that these odors be eliminated.

The process and composition of this invention is particularly suited to eliminating paper mill odors due to the ability of the compounds of Formulas I-III to react with odorous mercaptans.

In accordance with the broadest aspects of the paper mill sludge segment of this invention paper mill sludge can be treated with a solution of a compound of Formulas I-III.

The preferred solvent is water, however, other solvents can be used. The solution which are used to treat Kraft paper mill sludge can have a concentration of from about 3 to about 5 percent with a more preferred range being from about 5 to about 12 percent with a most preferred concentration being 8 percent. All concentrations are by weight.

For treating paper mill sludge is preferred that the solution be buffered to a pH of about 9.

While a wide variety of buffering agents can be used, a preferred buffering agents are potassium and sodium biocarbonate.

Further the solution may incorporate a wetting agent, it is preferred that the solution incorporate a nonionic wetting agent at a concentration of from about 0.1 to about 5 weight percent. The caveats and qualifications for wetting agents as are discussed above likewise apply for the treatment of paper mill sludges. The preferred wetting agent for use in conjunction with paper mill sludge treating compositions is an anionic wetting agent sold under the trademark Avanel S-74 by the BASF Chemical Co. of Mt. Olive, N.J. The applicant believes that Avanel S-74 is Ethoxylated ROH sulfonate, where R is $Ch_3$, $CH_3\ CH_2$ or $CH_3\ CH_2\ CH_2$.

Biocidal Activity

The compounds of Formulas I-III exhibit excellent biocidal activity against a wide variety of bacteria. This ability to kill bacteria lends the compounds of Formulas I-III to a wide variety of usages i.e. usage in soaps, use as a drug for diseased cultural fish and usage as a bovine teat cleaner in the dairy arts etc.

For testing against Straph Epi, E Coli, VRE, MRSA, PSEVDO and Strep Gp A bacteria an aqueous solution of 0.8 percent, of the compound of Formula III was prepared. The solution further incorporated 0.2 percent sodium biocarbonate and 0.1 percent of an anionic wetting agent sold under the trademark Avenal S 74 was prepared, all percentages are weight percentages. The wetting agent Avenel S-74 is described in detail herein above.

The compound of Formula III was tested against various bacteria.

In these test solutions were sprayed on the specified bacteria cultures, the results of the test are as specified in Tables I-III and FIG. 1-7. All results are raw count.

| | Number of CFU's per plate | | | | | |
|---|---|---|---|---|---|---|
| | Staph Epi | E coli | VRE | MRSA | Pseudo | Strep Gp A |
| Control | 3700 | 480 | 2200 | 3300 | 450 | 1900 |
| 10 min | 0 | 0 | 0 | 0 | 0 | 0 |
| 5 min | 0 | 0 | 0 | 0 | 0 | 0 |
| 1 min | 15 | 0 | 190 | 26 | 0 | 530 |
| 30 Sec | 420 | 0 | 410 | 290 | 0 | 590 |
| 5 Sec | 3400 | 63 | 1300 | 1100 | 202 | 770 |

TABLE II

| | Percent Survival | | | | | |
|---|---|---|---|---|---|---|
| | Staph Epi | E coli | VRE | MRSA | Pseudo | Strep GpA |
| 10 min | 0 | 0 | 0 | 0 | 0 | 0 |
| 5 min | 0 | 0 | 0 | 0 | 0 | 0 |
| 1 min | .4 | 0 | 8.6 | .8 | 0 | 27.9 |
| 30 Sec | 11.3 | 0 | 18.6 | 8.8 | 0 | 31.1 |
| 5 Sec | 91.9 | 13.1 | 59.1 | 33.3 | 44.9 | 40.5 |

TABLE III

| | Percent Kill | | | | | |
|---|---|---|---|---|---|---|
| | Staph Epi | E coli | VRE | MRSA | GpA | Strep GpA |
| 10 min | 100 | 100 | 100 | 100 | 100 | 100 |
| 5 min | 100 | 100 | 100 | 100 | 100 | 100 |
| 1 min | 99.6 | 100 | 91.4 | 99.2 | 100 | 72.1 |
| 30 Sec | 88.7 | 100 | 81.4 | 91.2 | 100 | 68.9 |
| 5 Sec | 81 | 869 | 40.9 | 66.7 | 55.1 | 59.5 |

The test protocol for the test of Tables I-III was as follows,
1. Dry uls of a 0.5 Macfarland suspension of a fresh bacterial growth onto a 22×22 glass cover slip.
2. Spray composition on cover slips.
3. Transfer cover slip to 5 ml of broth and shake for 10 seconds.
4. Using a 10 ul loop, streak the broth onto a blood agar plate.
5. Incubate 24 hours at 35 c.
6. Perform colony count.
7. All testing will be performed in duplicate.

8. The controls will be handled in the same manner as the test slide except the controls will not be sprayed with composition of Formula III.
9. Calculate the percentage kill for each time interval by dividing the testing count by the control count.

As can be seen from the data of Tables I-III and FIGS. 1-6 all bacterial activity ceased in five minutes, with all bacterial activity essentially being terminated in one minute.

The data of Tables I-III demonstrates that the compound of Formula III is an outstanding biocide. This ability to kill a wide variety of bacteria can be put to good use in a wide variety of applications.

Figure 1:
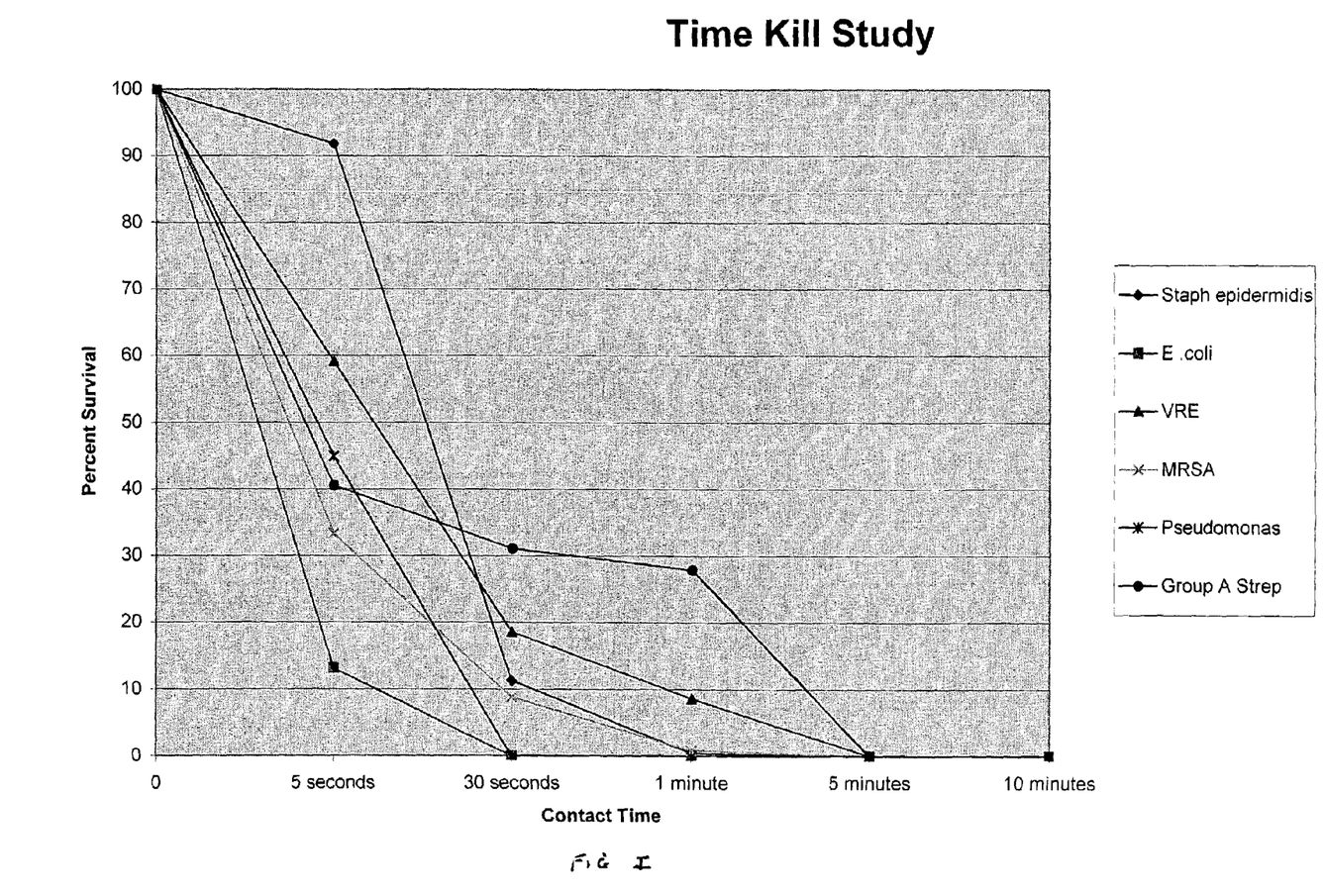
FIG. 1 is a graphic representation of time kill studies on a plurality of bacteria.
Figure 2:
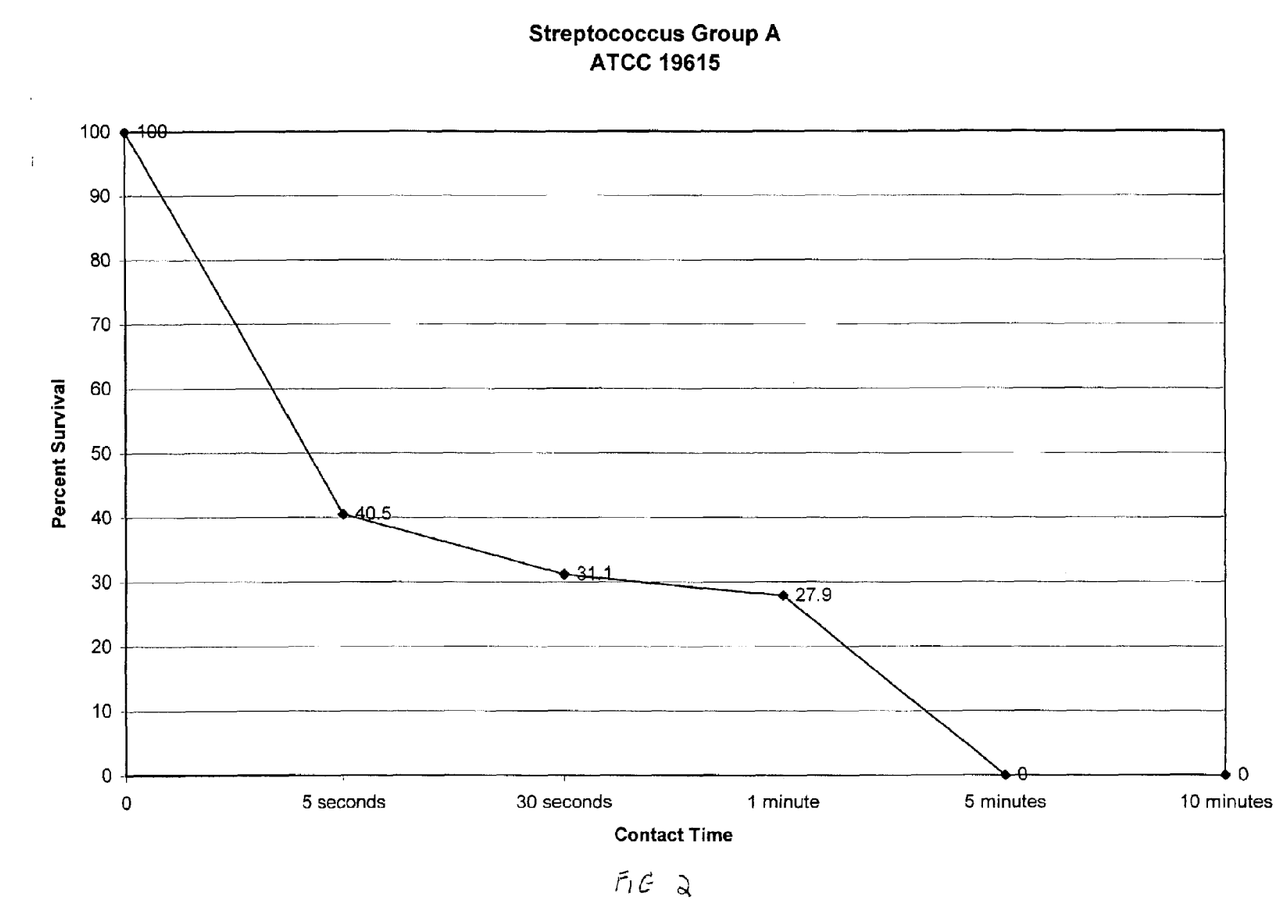
FIG. 2 is a graphic representation of time kill studies for Streptococcus Group A.
Figure 3:
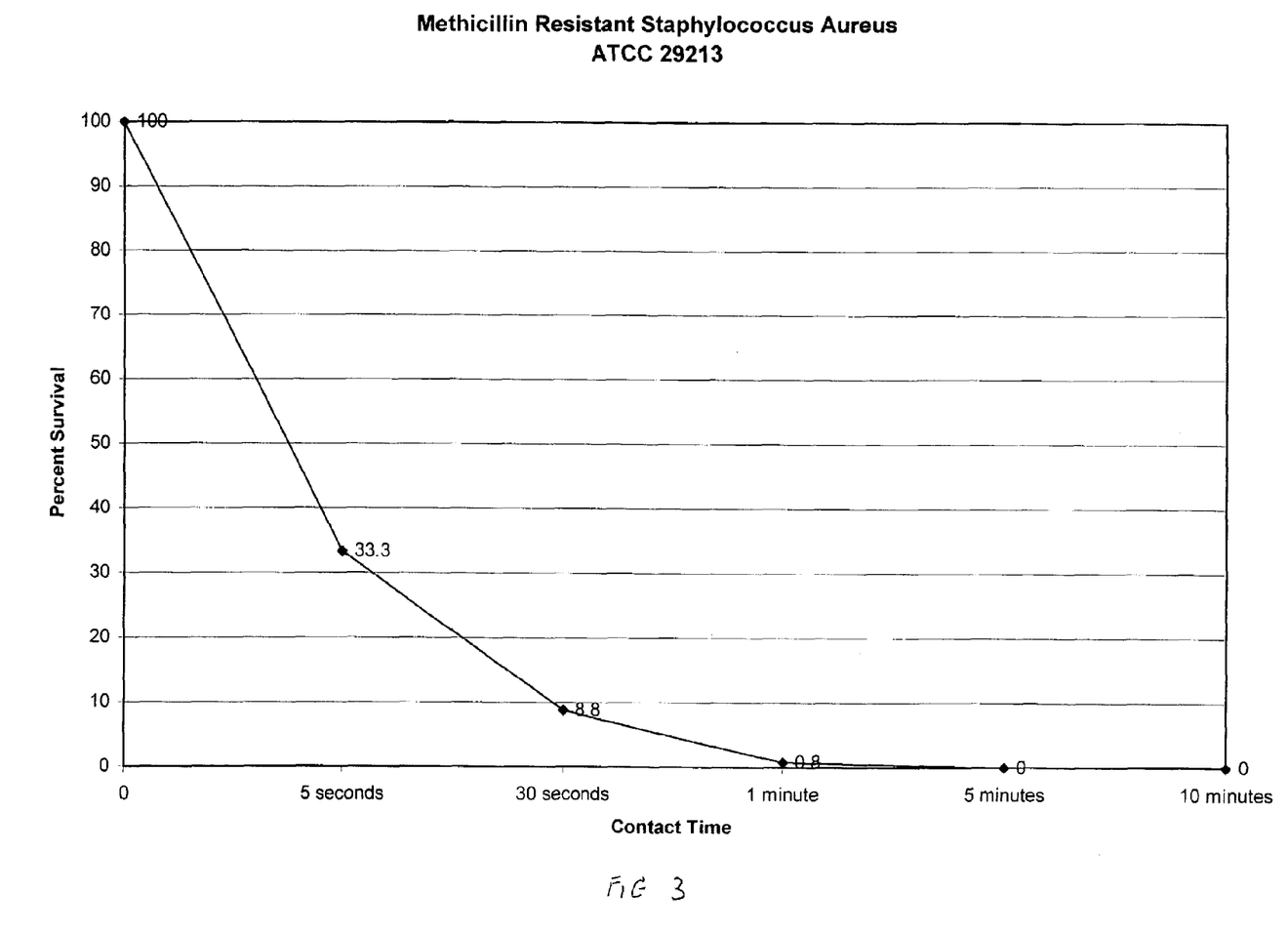
FIG. 3 is a graphic representation of time kill studies for Methicillin Resistant *Staphylococcus Aureus*.
Figure 4:
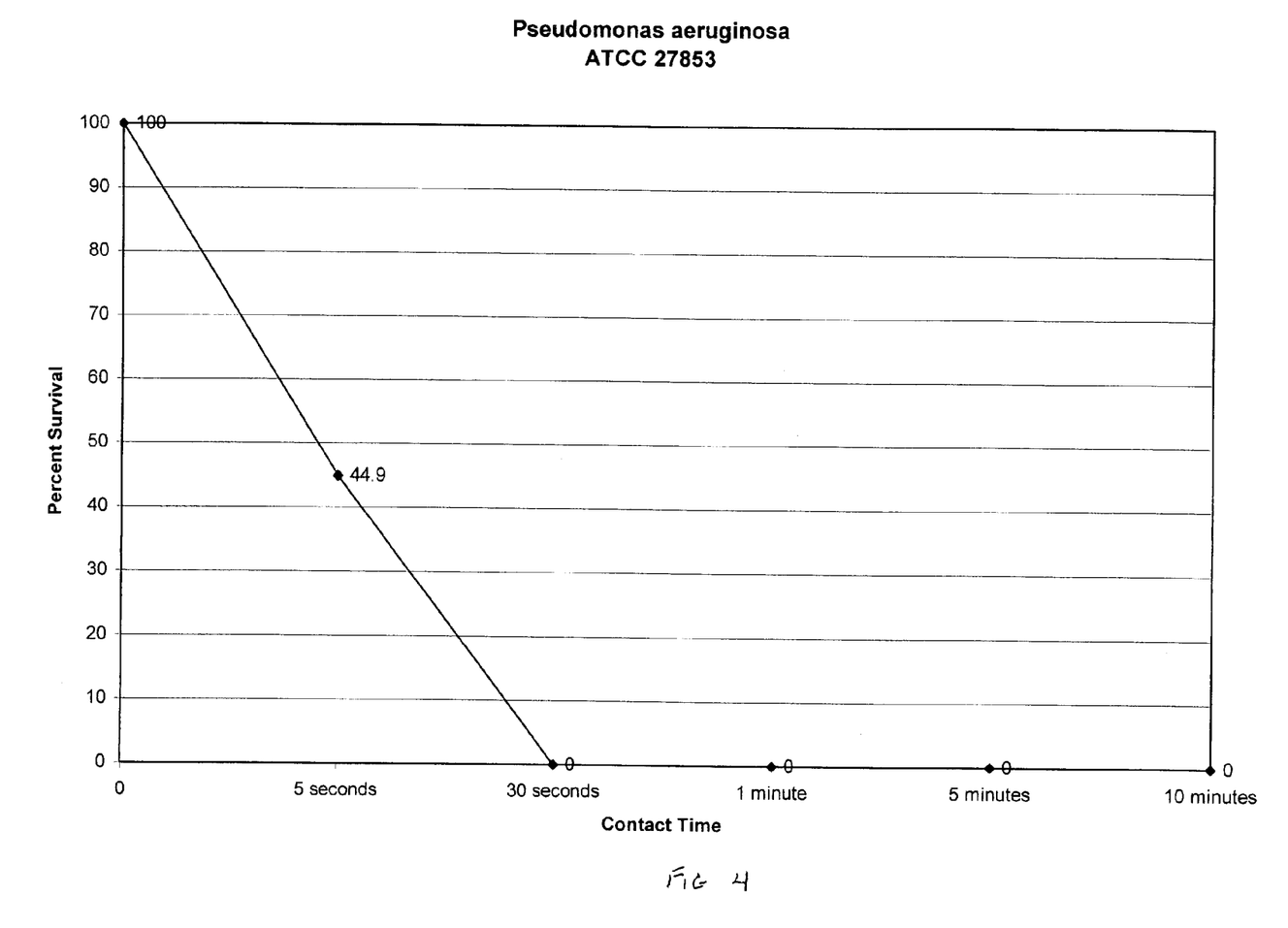
FIG. 4 is a graphic representation of time kill studies on *Pseudomonas Aeruginosa*.
Figure 5:
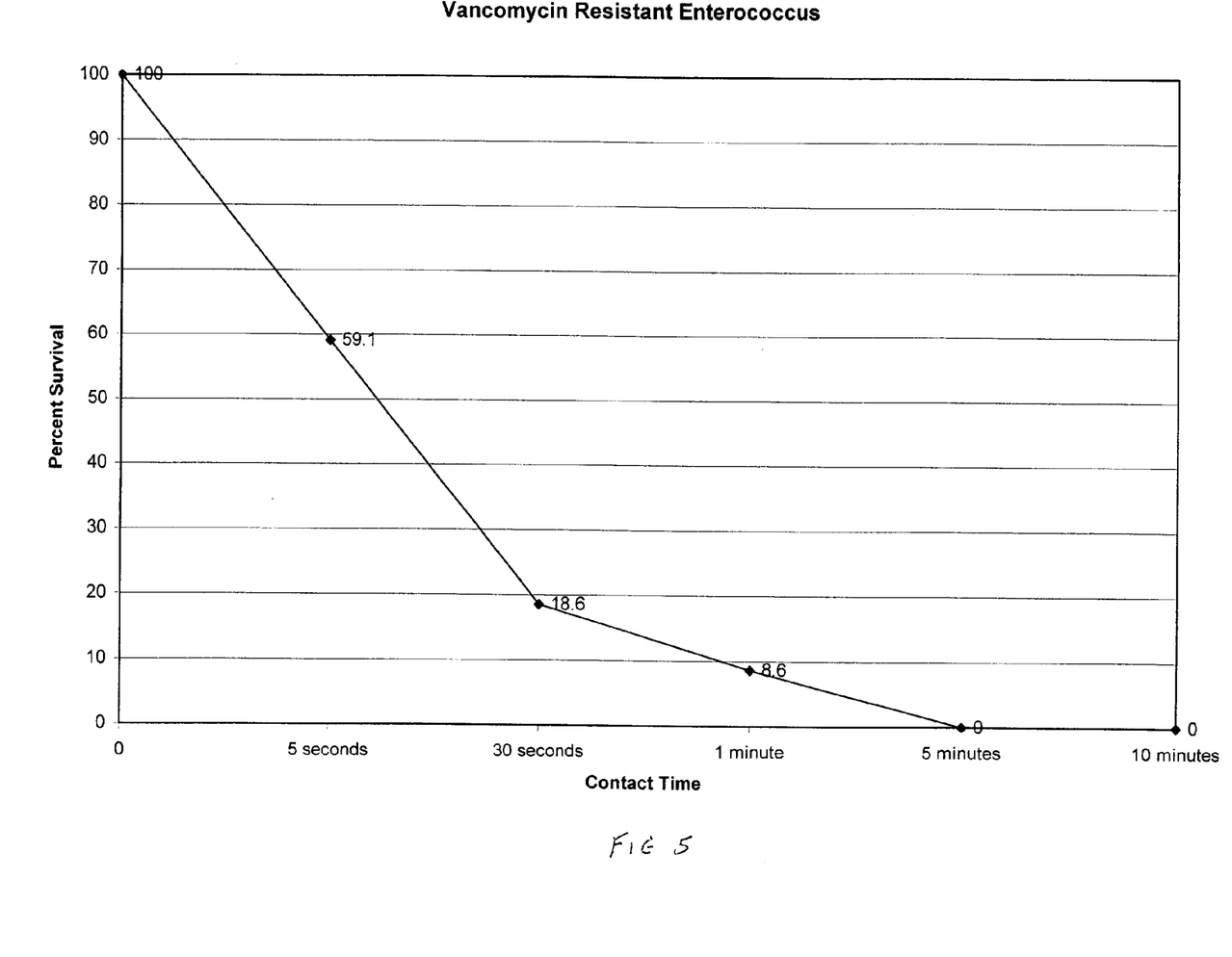
FIG. 5 is a graphic representation of time kill studies on Vancomycin Resistant Enterococcus.
Figure 6:
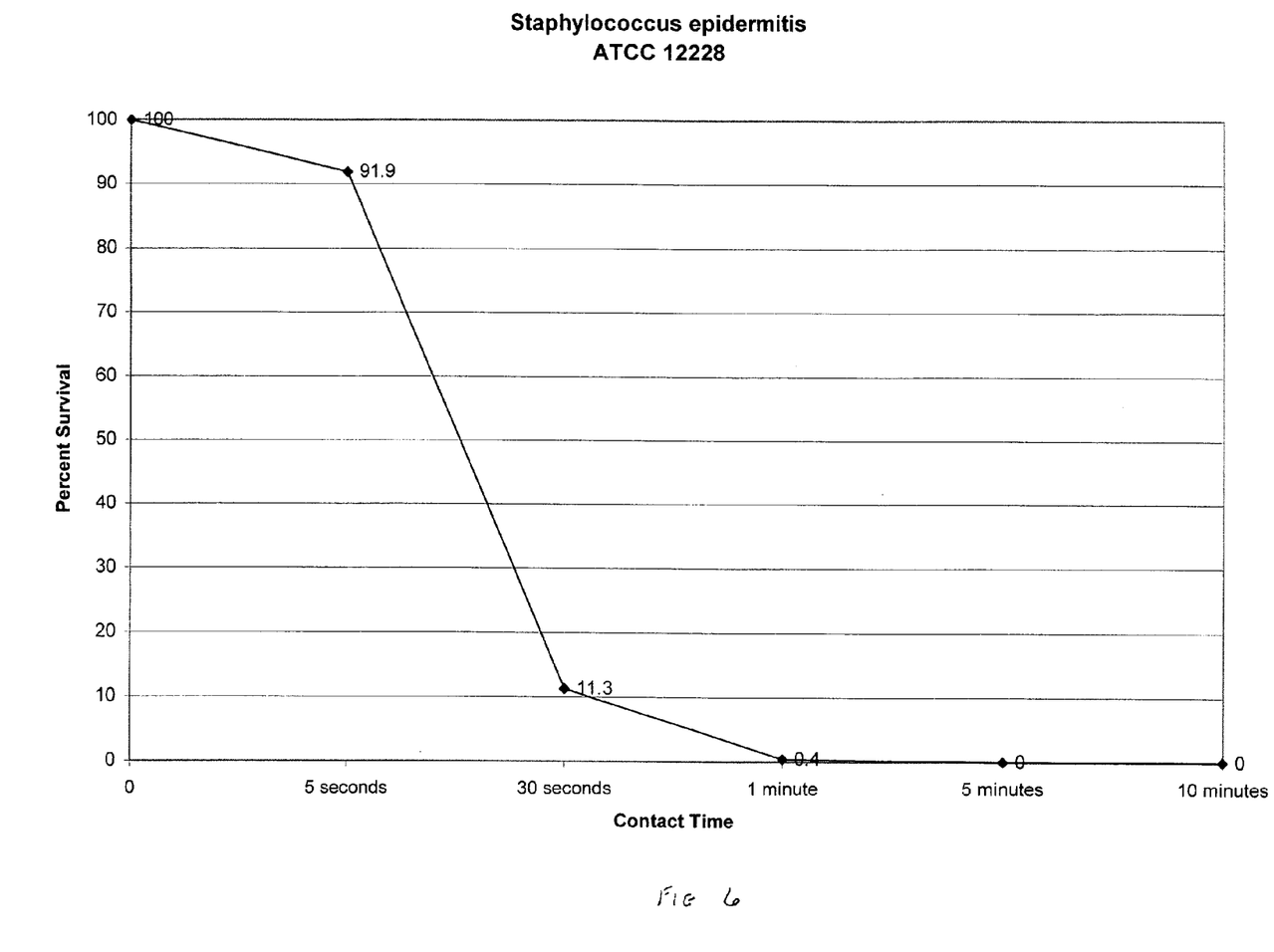
FIG. 6 is a graphic representation of time kill studies on *Staphylococcus Epidermitis*.
Figure 7:
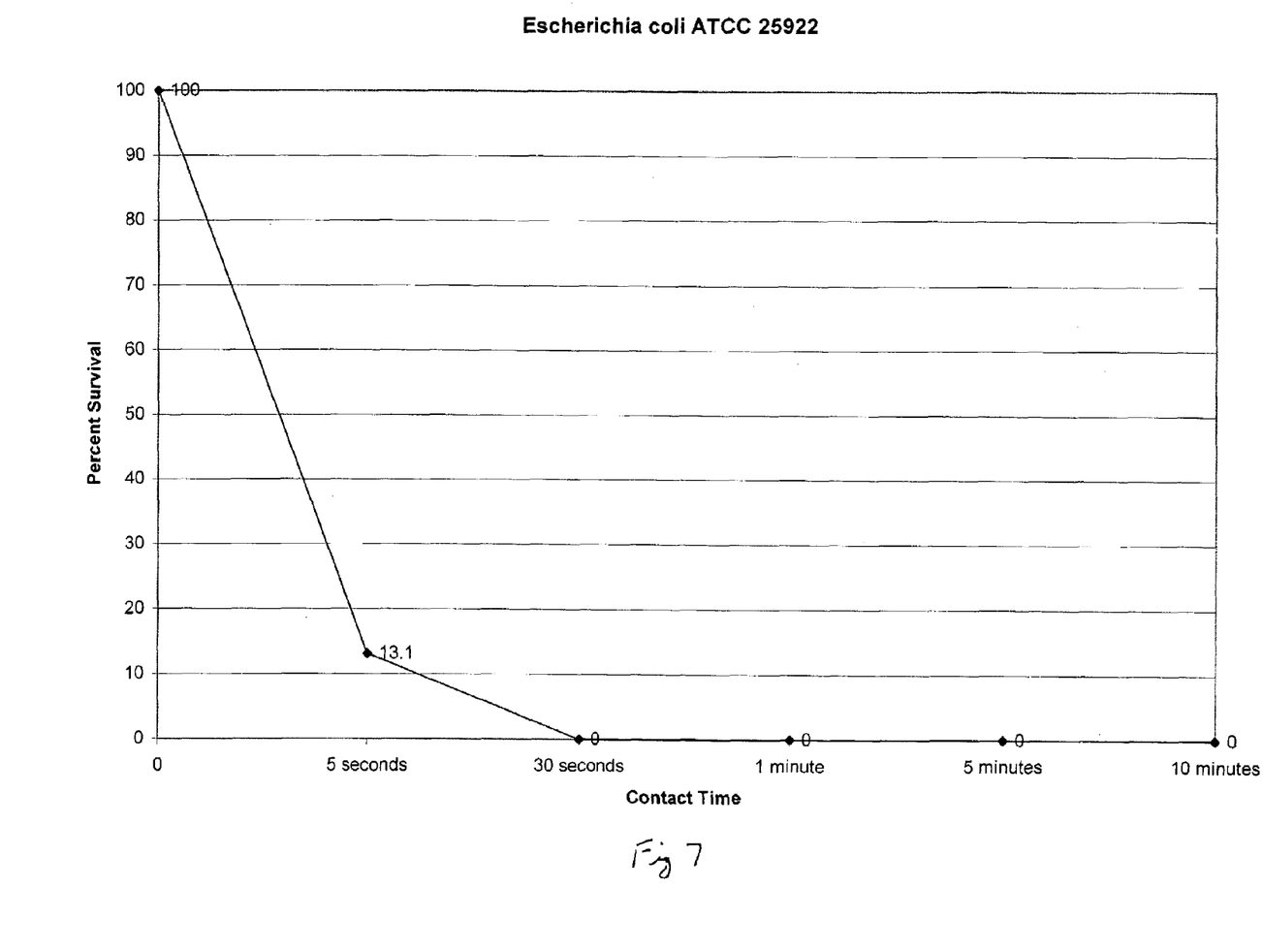
FIG. 7 is a graphic representation of time kill studies on *Escherichia Coli*.

FIG. 1 is a graphic representation of the data which is the subject of Tables I-III. From FIG. 1 it can be seen that all bacterial activity ceases in approximately one minute, with most bacterial activity being terminated in less than one minute.

While the new halo active aromatic sulfonamide compounds of Formulas I-III are extremely toxic for bacteria, this property would be of little advantage if these compounds were toxic for mammals. In this connection single dose oral toxicity test was conducted on rats. A 1% solution of the compound of Formulas III was administered to ten healthy male Wistar Albino rats. These rats were dosed orally at a dosage rate of 5000 mg/kg of body weight. The rats were not fed for a period of 16-20 hrs prior to dosage and water was freely available at all times. After dosage the rats were observed 3-4 hours post dosage and daily for 14 days thereafter. None of the rats exhibited toxicity or pharmacological effects. If less than one half of the animals die at a dose of 5000 mg/kg a substance is considered to be non toxic in accordance with 16 CFR 1500.3 (C) (2)(i)

In accordance with this test the compound of Formula III is considered to be non toxic for mammals and hence it is safe to use the compound of Formula III as a biocide in proximity to humans.

Likewise, the compounds of Formulas I-III are nontoxic to aquatic life. This fact is discussed in greater detail herein below.

Further the compounds of Formulas I-III have minimal long term effects on the environment as they degrade in one to thirty days when exposed to the atmosphere and/or sunlight. As a result of this property the compounds of Formulas I-III have no detrimental long term effects on the Eco system. This property is practically important to wildlife as the compounds of Formulas I-III do not have a chance to accumulate in mammals, bird or aquatic life. Likewise the degradation byproducts of the compounds of Formulas I-III are non toxic to wildlife.

Fungicidal Usages

The compounds of Formulas I-III are excellent fungicides. This property makes these compounds particularly suitable for use as additives in paint formulations.

The build up of mold and algae on painted surfaces is a problem particularly in southern climates. In order to prevent these build ups fungicides are often added to paint formulations. The compounds of Formulations I-III have excellent water solubility and hence these compounds can be easily blended into water based paint formulations.

Further if the compounds of Formulas I-III are modified by making $R_1$ a long chain fatty molecules of about C12 the solubility in oil based formulations, i.e. oil based paints, can be enhanced.

In paint formulations concentrations of about 0.1 to about 5 weight percent have been found to be useful in preventing the build up fungi on painted surfaces.

Biocidal Soap

Biocidal soaps are common in the medical arts. For general use biocidal soaps are likewise advantageous. As can be seen from the above set forth Tables I to III the compounds of Formulas I-III have excellent biocidal properties.

The most common biocidice for use in soaps is triclosan. While this compound has good biocidal properties its usage is troublesome for environmental reason because it does not degrade and hence tends to accumulate in the eco system. This accumulation in the eco system has been found to be troublesome to bird life.

Due to their excellent solubility in water the compounds of Formulas I-III can easily be formulated into water based soap formulations. Further for oil based soaps the solubility of the compounds of Formulas I-III can be enhanced by allowing $R_1$ to become a fatty acid chain of about $C_{12}$.

As is set forth in Tables I-III herein above the new sulfonamide compounds of this invention have excellent biocidal properties against a broad spectrum of bacteria.

The use of the compounds of Formulas I-III in soap formulations is useful for purposes of killing bacteria in order to prevent the spread of diseases.

Further the compounds of Formulas I-III are useful in deodorant type soaps which may further contain a perfume. The perfume is used to impart a pleasant smell to the user while the sulfonamide compound of this invention is used to prevent future bacterial growth on the skin of the user. This bacterial growth on a human results in what is referred to as body odor.

Soap formulation can contain from about 0.1 to about 10 weight percent of a sulfonamide compound as is defined by Formulas I-III. A more preferred range is from about 0.5 to about 5 weight percent, with a most preferred range being from about 0.75 to about 1.5 weight percent. One skilled in the art understands that the exact concentration of the sulfonamide additive depends on the soap formulation and on the particular additive utilized.

Curing Diseases in Cultured Fish

Sulfonamide compounds in the form of Chloramine T have been used, for decades, to cure diseases in cultured fish. The diseases cured are bacterial infections in the gills of fish which are contained in a rearing pond.

While Chloramine T is an effective drug for this purpose it has draw backs in that Chloramine T can be very toxic to cultured fish if the dosage is improper.

One embodiment of this invention is concerned with a process for disease control or curing fish which are from suffering PGD. PGD is a term used to refer to a plurality of diseases, which are caused by exposure of the fish to gamma negative bacteria, myxobacteria, alromonads and pseudomonods. PGD results from crowding in the ponds or tanks which are used to contain the fish, once started a disease can spread rapidly causing the loss of millions of fish as may be contained in a tank or pond. In the subject invention a drug which is a compound of Formulas I-III is administered by preparing a solution of the compound and allowing the diseased fish to swim in this solution.

Fish which are diseased with PGD tend to stop eating, lose their orientation and float on their side. If action is not taken immediately the whole population of the tank or pond can be dead within 24 to 48 hours. In accordance with this invention diseased fish are cured by allowing these fish to swim in a solution of a compound of Formulas I-III.

While Chloramine T has been used in the past to treat fish which are afflicted with PGD, the use of Chloramine T is difficult as if the dosages of Chloramine T are not carefully controlled the Chloramine T will kill the fish which are being treated.

The compounds of Formulas I-III exhibit minimal toxicity to fish. In order to test this toxicity healthy catfish were exposed to the compound of Formula III for three hours. The catfish were allowed to swim in solutions wherein the concentration of the compound of Figure III was 20, 40, 60, 80 and 100 ppm. After three hours all of the fish were healthy and exhibited no signs of stress. As a control catfish as described above were exposed to the prior art Chloramine T at concentrations of 80 and 100 ppm. At the end of the three hours exposure all of the catfish were dead.

The above description and drawings are illustrative of modifications that can be made without departing from the present invention, the scope of which is to be limited only by the following claims.

What is claimed is:

1. A process for eliminating the odor in an substrate which comprises the steps of treating the substrate with an effective amount of a solution of a halo active aromatic sulfonamide organic compound having the following structure;

Wherein,
$R_1$ is COOH,
X is chlorine, fluorine, bromine or iodine; and
M is sodium or potassium.

2. The process of claim 1 wherein,
M is sodium,
X is chlorine, and
$R_1$ is COOH.

3. A process for sanitizing the teats of a bovine which comprises applying to the teat of a solution containing an effective amount of a halo active aromatic sulfonamide organic compound having the following structure;

wherein,
X is a halogen;
$R_1$ is COOH; and
M is sodium or potassium.

4. A process for killing bacteria or fungi as may be contained on a substrate which comprises treating the substrate with an effective amount of a halo active aromatic sulfonamide organic compound having the following structure;

wherein,
$R_1$ is COOH or COOM,

X is chlorine and
M is sodium.

5. The process of claim 1 wherein the concentration of the halo active aromatic sulfonamide organic compound in the solution is from about 0.01 to about 20 weight percent.

6. The process of claim 1 wherein the concentration of the halo active aromatic sulfonamide organic compound in the solution is from about 0.1 to about 5 weight percent.

7. The process of claim 1 wherein the concentration of the halo active aromatic sulfonamide organic compound in the solution is from about 0.5 to about 1 weight percent.

8. The process of claim 2 wherein the concentration of the halo active aromatic sulfonamide organic compound in the solution is from about 0.01 to about 20 weight percent.

9. The process of claim 2 wherein the concentration of the halo active aromatic sulfonamide organic compound in the solution is from about 0.1 to about 5 weight percent.

10. The process of claim 2 wherein the concentration of the halo active aromatic sulfonamide organic compound in the solution is from about 0.5 to about 1 weight percent.

11. The process of claim 3 wherein the concentration of the halo active aromatic sulfonamide organic compound in the solution is from about 0.01 to about 20 weight percent.

12. The process of claim 3 wherein the concentration of the halo active aromatic sulfonamide organic in the solution is from about 0.1 to about 5 weight percent.

13. The process of claim 3 wherein the concentration of the halo active aromatic sulfonamide organic compound in the solution is from about 0.5 to about 1 weight percent.

14. The process of claim 4 wherein the concentration of the halo active aromatic sulfonamide organic compound in the solution is from about 0.01 to about 20 weight percent.

15. The process of claim 4 wherein the concentration of the halo active aromatic sulfonamide organic compound in the solution is from about 0.1 to about 5 weight percent.

16. The process of claim 4 wherein the concentration of the halo active aromatic sulfonamide organic compound in the solution is from about 0.5 to about 1 weight percent.

17. A process for curing cultural fish of bacterial infections which comprises allowing the diseased fish to swim for an effective period of time, in a solution containing an effective amount of an halo active aromatic sulfonamide organic compound having the following structure;

wherein,
X is halogen,
$R_1$ is COOH;
and M is sodium or potassium.

18. The process of claim 17 wherein the concentration of the halo active aromatic sulfonamide compound is from about 50 to about 600 ppm.

19. The process of claim 17 wherein the concentration of the halo active aromatic sulfonamide compound is from about 100 to about 400 ppm.

20. The process of claim 17 wherein the concentration of the halo active aromatic sulfonamide compound is from about 150 to about 250 ppm.

21. The process of claim 20 wherein the concentration of the halo active aromatic sulfonamide organic compound is about 200 ppm.

22. The process of claim 21 wherein the exposure time is about from about 10 to about 120 minutes.

23. The process of claim 22 wherein the exposure time is from about 30 to about 90 minutes.

24. A biocidal soap which contains an effective amount of a halo active aromatic sulfonamide compound having the following formula:

wherein,
$R_1$ is COOH or COOM,
X is chlorine, and
M is sodium.

25. The biocidal soap of claim 24 wherein the concentration of halo active aromatic sulfonamide organic compound is from about 0.1 to about 10 weight percent.

26. The biocidal soap of claim 25 wherein the concentration of halo active aromatic sulfonamide organic compound is from about 0.5 to about 2 weight percent.

27. The biocidal soap of claim 26 wherein the concentration of the halo active aromatic sulfonamide organic compound is about 0.75 weight percent.

28. A process for removing a stain, as contained on a textile substrate which comprises treating the substrate with an effective amount of a halo active aromatic sulfonamide organic compound having the following structure;

wherein,
X is a halogen,
$R_1$ is COOH; and
M is sodium or potassium.

* * * * *